US009410099B2

(12) United States Patent
D'Amore et al.

(10) Patent No.: US 9,410,099 B2
(45) Date of Patent: *Aug. 9, 2016

(54) PROCESS FOR MAKING ISOOCTENES FROM AQUEOUS ISOBUTANOL

(71) Applicant: Butamax Advanced Biofuels LLC, Wilmington, DE (US)

(72) Inventors: Michael B. D'Amore, Wilmington, DE (US); Leo Ernest Manzer, Wilmington, DE (US); Edward S. Miller, Jr., Knoxville, TN (US); Jeffrey P. Knapp, Wilmington, DE (US)

(73) Assignee: Butamax Advanced Biofuels LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/749,095

(22) Filed: Jun. 24, 2015

(65) Prior Publication Data

US 2015/0291900 A1    Oct. 15, 2015

Related U.S. Application Data

(63) Continuation of application No. 13/967,696, filed on Aug. 15, 2013, which is a continuation of application No. 11/818,354, filed on Jun. 13, 2007, now abandoned.

(60) Provisional application No. 60/814,153, filed on Jun. 16, 2006.

(51) Int. Cl.
| *C07C 5/03* | (2006.01) |
| *C12P 5/02* | (2006.01) |
| *C07C 1/20* | (2006.01) |
| *C10L 1/16* | (2006.01) |
| *C10L 1/18* | (2006.01) |
| *C07C 9/21* | (2006.01) |
| *C07C 29/04* | (2006.01) |
| *C07C 41/06* | (2006.01) |
| *C07C 1/22* | (2006.01) |
| *C10L 1/182* | (2006.01) |
| *C10L 1/185* | (2006.01) |

(52) U.S. Cl.
CPC ... *C10L 1/16* (2013.01); *C07C 1/20* (2013.01); *C07C 1/22* (2013.01); *C07C 5/03* (2013.01); *C07C 9/21* (2013.01); *C07C 29/04* (2013.01); *C07C 41/06* (2013.01); *C10L 1/18* (2013.01); *C12P 5/026* (2013.01); *C07C 2521/08* (2013.01); *C07C 2527/054* (2013.01); *C07C 2529/18* (2013.01); *C07C 2529/40* (2013.01); *C07C 2531/10* (2013.01); *C10G 2300/4006* (2013.01); *C10G 2300/4012* (2013.01); *C10G 2300/805* (2013.01); *C10G 2400/22* (2013.01); *C10L 1/1608* (2013.01); *C10L 1/1824* (2013.01); *C10L 1/1852* (2013.01); *C10L 2200/0469* (2013.01); *C10L 2270/023* (2013.01); *C10L 2270/026* (2013.01); *C10L 2270/04* (2013.01); *C10L 2290/26* (2013.01)

(58) Field of Classification Search
None
See application file for complete search history.

(56) References Cited

U.S. PATENT DOCUMENTS

| 2,228,662 | A | * | 1/1941 | Holm | C10L 1/023 44/356 |
| 3,481,718 | A | * | 12/1969 | Schoen | C10L 1/14 44/375 |
| 3,687,644 | A | * | 8/1972 | Delafield | C10L 1/14 44/329 |
| 4,292,219 | A | * | 9/1981 | Lyons | C07C 43/04 524/369 |
| 4,338,469 | A | * | 7/1982 | Lyons | C07C 41/06 106/316 |
| 4,374,859 | A | | 2/1983 | Kunkee et al. | |
| 4,450,294 | A | | 5/1984 | Feldman | |
| 4,628,116 | A | | 12/1986 | Cenedella | |
| 5,288,924 | A | | 2/1994 | Beech et al. | |
| 5,755,967 | A | | 5/1998 | Meagher et al. | |
| 6,358,717 | B1 | | 3/2002 | Blaschek et al. | |
| 6,716,258 | B2 | * | 4/2004 | Yeh | C10L 1/026 44/388 |
| 7,993,889 | B1 | | 8/2011 | Donaldson et al. | |
| 2002/0045786 | A1 | | 4/2002 | Gammersbach et al. | |
| 2003/0018228 | A1 | * | 1/2003 | Vaughn | C08F 10/00 585/500 |
| 2004/0267066 | A1 | * | 12/2004 | Smith | C07C 2/66 585/323 |
| 2005/0054861 | A1 | | 3/2005 | Manzer | |
| 2005/0089979 | A1 | | 4/2005 | Ezeji et al. | |
| 2005/0112739 | A1 | | 5/2005 | Golubkov | |
| 2005/0233423 | A1 | | 10/2005 | Berka et al. | |
| 2007/0259411 | A1 | | 11/2007 | Bramucci | |
| 2008/0131948 | A1 | | 6/2008 | Manzer et al. | |
| 2008/0220488 | A1 | | 9/2008 | D'Amore et al. | |
| 2014/0005443 | A1 | | 1/2014 | D'Amore et al. | |
| 2014/0030794 | A1 | | 1/2014 | Donaldson et al. | |

FOREIGN PATENT DOCUMENTS

| EP | 0088602 A2 | 9/1983 |
| EP | 0263403 A2 | 4/1988 |
| EP | 0263403 B1 | 4/1988 |

(Continued)

OTHER PUBLICATIONS

Zambonelli et al., "Autolysogeny and High Isobutyl Alcohol Production in *Saccharomyces cerevisiae*", Current Microbiology, vol. 23, 1991, pp. 281-283.
A. D. Petroff et al., De La Structure Du Di-Isobutylene De Malbot, Bulletin De La Societe Cjimique De France, 1933, vol. 53:327-330.
Doherty et al., Conceptual Design of Distillation Systeyems, 2001, pp. 365-366, McGraw-Hill New York.
Ramey et al, Production of Butyric Acid and Butanol From Biomass, Final Report of Work Performed Under U.S. Department of Energy DE-F-G02-00ER86106, 57-58.
Prosecution of U.S. Appl. No. 13/839,246, U.S. Published Patent Application 2014/0030794, filed Mar. 15, 2013.

(Continued)

*Primary Examiner* — Rosalynd Keys

(57) ABSTRACT

The present invention relates to a catalytic process for making isooctenes using a reactant comprising isobutanol and water. The isooctenes so produced are useful for the production of fuel additives.

25 Claims, 7 Drawing Sheets

(56) References Cited

FOREIGN PATENT DOCUMENTS

| EP | 0263403 A3 | 6/1990 |
| EP | 0263403 B1 | 4/1993 |
| GB | 576480 | 4/1946 |
| GB | 576480 A | 4/1946 |
| WO | 9703932 A1 | 2/1997 |
| WO | 03031539 A1 | 4/2003 |

OTHER PUBLICATIONS

Anderson et al., Solid Acid and Base Catalysts, Catalysis: Science and Technology, 1981, vol. 2, 232-273, Springer-Verlag, New York.
Satterfield, C. N., "Catalyst Preparation and Manufacture", Heterogeneous Catalysis in Practice, 2.SUP.nd Edition, Chapter 4, 68-98, 1991, McGraw-Hill, New York.
Perry et al., Perry's Chemical Engineer's Handbook, 7.SUP.th Edition, Sections 13, 18, and 22 1997, McGraw-Hill, New York.
Augustine, R. L., "The Active Site", Heterogeneous Catalysis for the Synthetic Chemist, Section 3, 27-49, 1996, Marcel Decker, New York.
Meschcheryakov et al., Izvest Akad. Nauk S.S.S.R.,1950, 282-285.
Liu et al, "Separation of acetone—butanol—ethanol (ABE) from dilute aqueous solutions by pervaporation", Separation and Purification Technology, 42, 2005, 273-282.
Ingraham et al., "The Formation of Higher Aliphatic Alcohols by Mutant Strains of *Saccharomyces cerevisiae*" Archives of Biochemistry and Biophysics, vol. 88, 1960, 157-166.
Kirk Othmer Encyclopedia of Chemical Technology,"Butyl Alcohols", vol. 4, Published Online Apr. 2001, 393-402.
Adkins, H., "Dehydration of Alcohols Over Alumina", Journal of the American Chemical Society, vol. 47, 1925, 1163-1167.
Senderens, J. B., Chimique Organique. Deshydration Catalytique, En Phase Gazeuse, Des Alcools Formeniquies En Presence Des Bisulfates Alcalins, Comptes Rendus Hebdomadaires Des Seances De L'Academie Des Sciences, vol. 190, 1930, 1167-1170.
Prosecution of U.S. Appl. No. 13/838,949, U.S. Published Patent Application 2014/0051151, filed Mar. 15, 2013.
Examination of IPR 2014-00143; entitled Renewable Compositions; U.S. Pat. No. 8,378,160; including, but not limited to, Petition for Inter Pules Review filed Nov. 11, 2013.
Examination of IPR 2014-00142; entitled Renewable Compositions; U.S. Pat. No. 8,193,402; including, but not limited to, Petition for Inter Partes Review filed Nov. 11, 2013.
Examination of IPR 2014-00144, entitled Renewable Compositions; U.S. Pat. No. 8,487,149; including, but not limited to, Petition for Inter Partes Review filed Nov. 11, 2013.
Prosecution of U.S. Appl. No. 11/586,315, filed Oct. 25, 2006 (U.S. Pat. No. 7,851,188), including, but not limited to, IPRs 95/001,718 and 95/001,857.
Prosecution of U.S. Appl. No. 12/103,844, filed Apr. 16, 2008, (U.S. Pat. No. 7,910,342).
Prosecution of U.S. Appl. No. 12/018,216, filed Jan. 23, 2008, (U.S. Pat. No. 7,993,889) including, but not limited to, IPRs 95/001,735 and 90/012,503.
Prosecution of U.S. Appl. No. 13/205,351, filed Aug. 8, 2011, (U.S. Pat. No. 8,178,328) including, but not limited to, IPR 95/001,998.
Prosecution of U.S. Appl. No. 12/966,333, filed Dec. 13, 2010, (U.S. Pat. No. 8,273,558).
Prosecution of U.S. Appl. No. 12/939,284, filed Nov. 4, 2010, (U.S. Pat. No. 8,283,144).
Prosecution of U.S. Appl. No. 13/539,125, filed Jun. 29, 2012.
Prosecution of U.S. Appl. No. 13/646,097, filed Oct. 5, 2012.
Prosecution of U.S. Appl. No. 12/939,315, filed Nov. 4, 2010.
Office Action, mailed Jun. 3, 2015, in U.S. Appl. No. 13/967,696, D'Amore, M.B., et al., filed Aug. 15, 2013.
Jean Baptiste Senderens: Chimique Organique. Deshydration Catalytique, En Phase Gaze Use, Des Alcools Formenioues En Presence Des Bisulfates Alcalins, Comptes Rendus Hebdomadaires Des Seances De L'Academie Des Sciences, 1930. vol. 190.1167-1170.
V. N. Ipatieff et al., The Dehydration of the Lower Aliphatic Alcohols in the Presence of Dilute Aqueous Solutions of Acids and Salts, Journal of the American Chemical Society, 1944, vol. 66:1627-1631.
Homer Adkins et al., Dehydration of Alcohols Over Alumina, Journal of the American Chemical Society. 1925, vol. 47:1163-1167.
D. Fritsch et al., Application of a Forced-Flow Catalytic Membrane Reactor for the Dimerisation of Isobutene, Catalysis Today, 2004, vol. 98;295-308.
International Search Report Dated Feb. 5, 2008, International Application No. PCT/US2007/014169, International Filing Date: Jun. 15, 2007.
Ernst Billig. Butyl Alcohols, Kirk-Othmer Encyclopedia of Chemical Tech., vol. 4, Published Online Apr. 16, 2001, pp. 393-402.
Liu et al., Separation and Purification Technology, vol. 42, 2005, pp. 273-282.
Zambonelli et al., Current Microbiology, vol. 23, 1991, pp. 281-283.
Ingraham et al., Archives of Biochemistry and Biophysics, vol. 88, 1960, pp. 157-166.

* cited by examiner

PROCESS FOR MAKING ISOOCTENES FROM AQUEOUS ISOBUTANOL

CROSS-REFERENCE TO RELATED APPLICATIONS

This application is a continuation of U.S. application Ser. No. 13/967,696, filed Aug. 15, 2013, which is a continuation of U.S. application Ser. No. 11/818,354, filed Jun. 13, 2007, which claims priority under 35 U.S.C. §119(e) from U.S. Provisional Application Ser. No. 60/814,153 (filed Jun. 16, 2006), the disclosures of each of which are incorporated by reference herein for all purposes as if fully set forth.

FIELD OF INVENTION

The present invention relates to a process for making isooctenes using aqueous isobutanol as a reactant.

BACKGROUND

Isooctenes are useful intermediates for the production of fuel additives. Isooctenes are typically produced from the reaction of isobutene or isobutene-containing hydrocarbon mixtures with an acid catalyst. U.S. Patent Application No. 2004/0054246, for example, describes the production of diisobutene from isobutene or mixtures comprising isobutenes using a solid acidic ion-exchange resin. U.S. Patent Application No. 2002/0045786 describes the preparation of diisobutylene from an isobutanol-containing raffinate using an acidic catalyst. Meshcheryakov, A. P., et al (Izvest. Akad. Nauk S.S.S.R. (1950) 282-285) describe the reaction of pure isobutanol in a sulfuric acid medium to produce di- and triisobutylenes.

Efforts directed at improving air quality and increasing energy production from renewable resources have resulted in renewed interest in alternative fuels, such as ethanol and butanol, that might replace gasoline and diesel fuel. Efforts are currently underway to increase the efficiency of isobutanol production by fermentative microorganisms with the expectation that renewable feedstocks, such as corn waste and sugar cane bagasse, could be used as carbon sources. It would be desirable to be able to utilize such isobutanol streams for the production of isooctenes, and for the further production of fuel additives from said isooctenes.

SUMMARY

The present invention relates to a process for making at least one isooctene comprising contacting a reactant comprising isobutanol and at least about 5% water (by weight relative to the weight of the water plus isobutanol) with at least one acid catalyst at a temperature of about 50 degrees C. to about 450 degrees C. and a pressure from about 0.1 MPa to about 20.7 MPa to produce a reaction product comprising said at least one isooctene, and recovering said at least one isooctene from said reaction product to obtain at least one recovered isooctene. In one embodiment, the reactant is obtained from fermentation broth.

The at least one recovered isooctene is useful as an intermediate for the production of transportation fuels and fuel additives. In particular, the at least one recovered isooctene can be converted to isooctanes, isooctanols or isooctyl alkyl ethers.

BRIEF DESCRIPTION OF THE DRAWING

The Drawing consists of seven figures.

DETAILED DESCRIPTION

Figure 1:
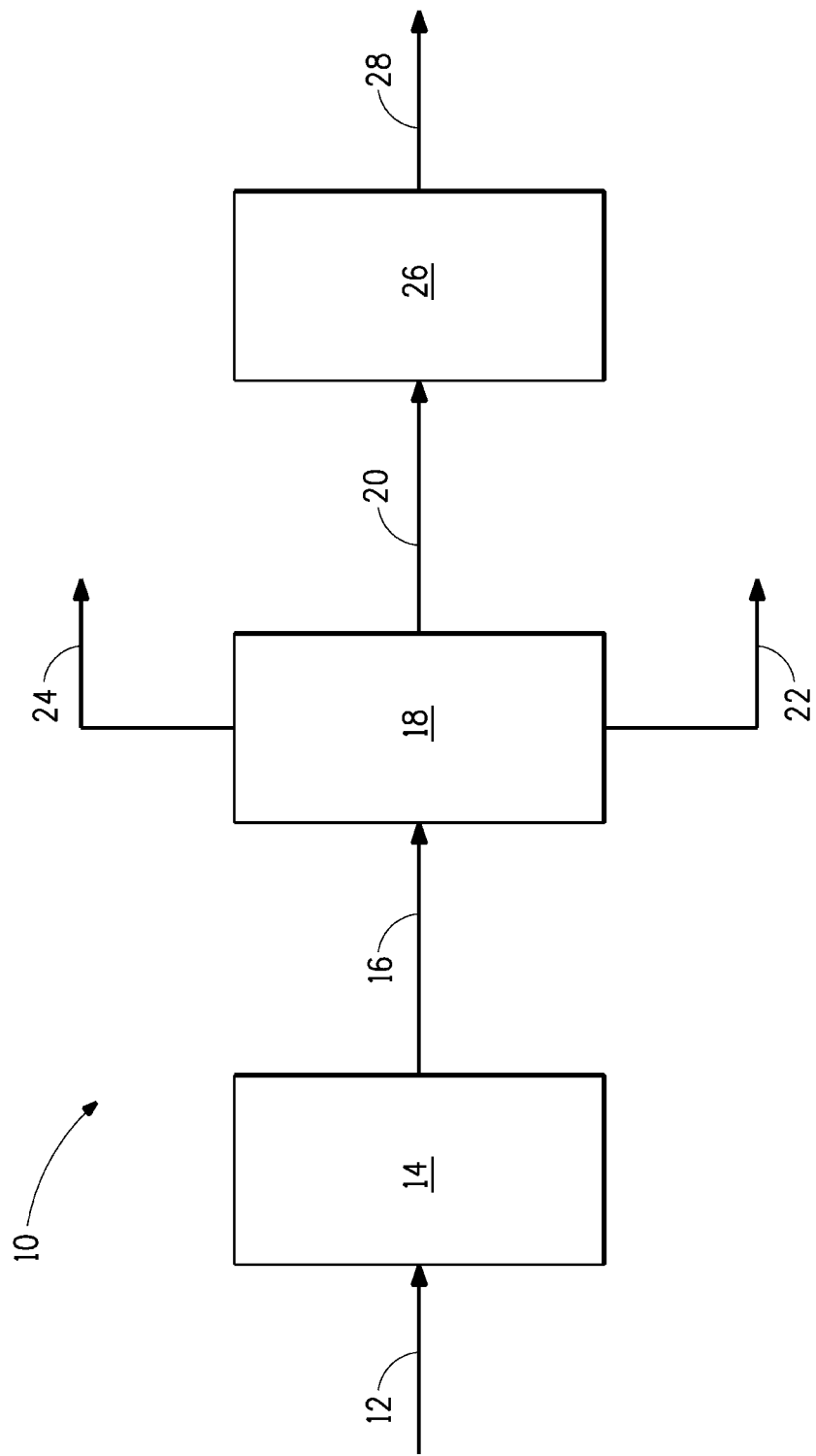
FIG. 1 illustrates an overall process useful for carrying out the present invention.

The present invention relates to a process for making at least one isooctene from a reactant comprising water and isobutanol. The at least one isooctene so produced is useful as an intermediate for the production of transportation fuels, wherein transportation fuels include, but are not limited to, gasoline, diesel fuel and jet fuel. The present invention further relates to the production of transportation fuel additives using isooctenes produced by the process of the invention.

In its broadest embodiment, the process of the invention comprises contacting a reactant comprising isobutanol and water with at least one acid catalyst to produce a reaction product comprising at least one isooctene, and recovering said at least one isooctene from said reaction product to obtain at least one recovered isooctene. By isooctene is meant any olefin having eight carbons, wherein at least one of the carbons is a secondary or tertiary carbon.

Although the reactant could comprise less than about 5% water by weight relative to the weight of the water plus isobutanol, it is preferred that the reactant comprise at least about 5% water. In a more specific embodiment, the reactant comprises from about 5% to about 80% water by weight relative to the weight of the water plus isobutanol.

In one preferred embodiment, the reactant is derived from fermentation broth, and comprises at least about 50% isobutanol (by weight relative to the weight of the isobutanol plus water) (sometimes referred to herein as "aqueous isobutanol"). One advantage to the microbial (fermentative) production of isobutanol is the ability to utilize feedstocks derived from renewable sources, such as corn stalks, corn cobs, sugar cane, sugar beets or wheat, for the fermentation process. Efforts are currently underway to engineer (through recombinant means) or select for organisms that produce isobutanol with greater efficiency than is obtained with current microorganisms. Such efforts are expected to be successful, and the process of the present invention will be applicable to any fermentation process that produces isobutanol at levels currently seen with wild-type microorganisms, or with genetically modified microorganisms from which enhanced production of isobutanol is obtained.

Isobutanol can be fermentatively produced by recombinant microorganisms as described in copending and commonly owned U.S. Pat. No. 7,851,188, page 5, line 9 through page 45, line 20, including the sequence listing. The biosynthetic pathway enables recombinant organisms to produce a fermentation product comprising isobutanol from a substrate such as glucose; in addition to isobutanol, ethanol is formed. The biosynthetic pathway enables recombinant organisms to produce isobutanol from a substrate such as glucose. The biosynthetic pathway to isobutanol comprises the following substrate to product conversions:
- a) pyruvate to acetolactate, as catalyzed for example by acetolactate synthase encoded by the gene given as SEQ ID NO:19;
- b) acetolactate to 2,3-dihydroxyisovalerate, as catalyzed for example by acetohydroxy acid isomeroreductase encoded by the gene given as SEQ ID NO:31;
- c) 2,3-dihydroxyisovalerate to α-ketoisovalerate, as catalyzed for example by acetohydroxy acid dehydratase encoded by the gene given as SEQ ID NO:33;
- d) α-ketoisovalerate to isobutyraldehyde, as catalyzed for example by a branched-chain keto acid decarboxylase encoded by the gene given as SEQ ID NO:35; and
- e) isobutyraldehyde to isobutanol, as catalyzed for example by a branched-chain alcohol dehydrogenase encoded by the gene given as SEQ ID NO:37.

Methods for generating recombinant microorganisms, including isolating genes, constructing vectors, transforming hosts, and analyzing expression of genes of the biosynthetic pathway are described in detail by Maggio-Hall, et al. in U.S. Pat. No. 7,851,188.

The biological production of butanol by microorganisms is believed to be limited by butanol toxicity to the host organism. Copending and commonly owned U.S. Pat. No. 7,659,104, page 5, line 1 through page 36, Table 5, and including the sequence listing (filed 4 May 2006) enables a method for selecting for microorganisms having enhanced tolerance to butanol, wherein "butanol" refers to 1-butanol, 2-butanol, isobutanol or combinations thereof. A method is provided for the isolation of a butanol tolerant microorganism comprising:
- a) providing a microbial sample comprising a microbial consortium;
- b) contacting the microbial consortium in a growth medium comprising a fermentable carbon source until the members of the microbial consortium are growing;
- c) contacting the growing microbial consortium of step (b) with butanol; and
- d) isolating the viable members of step (c) wherein a butanol tolerant microorganism is isolated.

The method of U.S. Pat. No. 7,659,104 can be used to isolate microorganisms tolerant to isobutanol at levels greater than 1% weight per volume.

Fermentation methodology is well known in the art, and can be carried out in a batch-wise, continuous or semi-continuous manner. As is well known to those skilled in the art, the concentration of isobutanol in the fermentation broth produced by any process will depend on the microbial strain and the conditions, such as temperature, growth medium, mixing and substrate, under which the microorganism is grown.

Following fermentation, the fermentation broth from the fermentor can be used for the process of the invention. In one preferred embodiment the fermentation broth is subjected to a refining process to produce an aqueous stream comprising an enriched concentration of isobutanol. By "refining process" is meant a process comprising one unit operation or a series of unit operations that allows for the purification of an impure aqueous stream comprising isobutanol to yield an aqueous stream comprising substantially pure isobutanol. For example, in one embodiment, the refining process yields a stream that comprises at least about 5% water and isobutanol, but is substantially free of ethanol and/or acetone that may have been present in the fermentation broth.

Refining processes typically utilize one or more distillation steps as a means for recovering a fermentation product. It is expected, however, that fermentative processes will produce isobutanol at very low concentrations relative to the concentration of water in the fermentation broth. This can lead to large capital and energy expenditures to recover the isobutanol by distillation alone. As such, other techniques can be used either alone or in combination with distillation as a means of concentrating the dilute isobutanol product. In such processes where separation techniques are integrated with the fermentation step, cells are often removed from the stream to be refined by centrifugation or membrane separation techniques, yielding a clarified fermentation broth. These cells are then returned to the fermentor to improve the productivity of the isobutanol fermentation process. The clarified fermentation broth is then subjected to such techniques as pervaporation, gas stripping, liquid-liquid extraction, perstraction, adsorption, distillation, or combinations thereof. Depending on product mix, these techniques can provide a stream comprising water and isobutanol suitable for use in the process of the invention. If further purification is necessary, the stream can be treated further by distillation to yield an aqueous isobutanol stream.

Separation Similarities of 1-butanol and Isobutanol

1-Butanol and isobutanol share many common features that allow the separation schemes devised for the separation of 1-butanol and water to be applicable to the isobutanol and water system. For instance both 1-butanol and isobutanol are equally hydrophobic molecules possessing log Kow coefficients of 0.88 and 0.83, respectively. Kow is the partition coefficient of a species at equilibrium in an octanol-water system. Based on the similarities of the hydrophobic nature of the two molecules one would expect both molecules to partition in largely the same manner when exposed to various solvent systems such as decanol or when adsorbed onto various solid phases such as silicone or silicalite. In addition, both 1-butanol and isobutanol share similar K values, or vapor-liquid partition coefficients, when in solution with water. Another useful thermodynamic term is α which is the ratio of partition coefficients, K values, for a given binary system. For a given concentration and temperature up to 100° C. the values for K and α are nearly identical for 1-butanol and isobutanol in their respective butanol-water systems, indicating that in evaporation type separation schemes such as gas stripping, pervaporation, and distillation, both molecules should perform equivalently.

The separation of 1-butanol from water, and the separation of 1-butanol from a mixture of acetone, ethanol, 1-butanol and water as part of the ABE fermentation process by distillation have been described. In particular, in a butanol and water system, 1-butanol forms a low boiling heterogeneous azeotrope in equilibrium with 2 liquid phases comprised of 1-butanol and water. This azeotrope is formed at a vapor phase composition of approximately 58% by weight 1-butanol (relative to the weight of water plus 1-butanol) when the system is at atmospheric pressure (as described by Doherty, M. F. and Malone, M. F. in Conceptual Design of Distillation Systems (2001), Chapter 8, pages 365-366, McGraw-Hill, New York). The liquid phases are roughly 6% by weight 1-butanol (relative to the weight of water plus 1-butanol) and 80% by weight 1-butanol (relative to the weight of water plus 1-butanol), respectively. In similar fashion, isobutanol also forms a minimum boiling heterogeneous azeotrope with water that is in equilibrium with two liquid phases. The azeotrope is formed at a vapor phase composition of 67% by weight isobutanol (relative to the weight of water plus isobutanol) (as described by Doherty, M. F. and Malone, M. F. in Conceptual Design of Distillation Systems (2001), Chapter 8, pages 365-366, McGraw-Hill, New York). The two liquid phases are roughly 6% by weight isobutanol (relative to the weight of water plus isobutanol) and 80% by weight isobutanol (relative to the weight of water plus isobutanol), respectively. Thus, in the process of distillative separation of a dilute 1-butanol and water or isobutanol and water system, a simple procedure of sub-cooling the azeotrope composition into the two phase region allows one to cross the distillation boundary formed by the azeotrope.

Distillation

For fermentation processes in which isobutanol is the predominant alcohol, aqueous isobutanol can be recovered by azeotropic distillation, as described generally in Ramey, D. and Yang, S.-T. (*Production of butyric acid and butanol from biomass*, Final Report of work performed under U. S. Department of Energy DE-F-G02-00ER86106, pages 57-58) for the production of 1-butanol. An aqueous isobutanol stream from the fermentation broth is fed to a distillation column, from which an isobutanol-water azeotrope is removed as a vapor phase. The vapor phase from the distillation column (comprising at least about 33% water (by weight relative to the weight of water plus isobutanol)) can then be used directly as the reactant for the process of the present invention, or can be fed to a condenser. Upon cooling, an isobutanol-rich phase (comprising at least about 16% water (relative to the weight of water plus isobutanol)) will separate from a water-rich phase in the condenser. One skilled in the art will know that solubility is a function of temperature, and that the actual concentration of water in the aqueous isobutanol stream will vary with temperature. The isobutanol-rich phase can be decanted and used for the process of the invention, and the water-rich phase preferably is returned to the distillation column.

For fermentation processes in which an aqueous stream comprising isobutanol and ethanol are produced, the aqueous isobutanol/ethanol stream is fed to a distillation column, from which a ternary isobutanol/ethanol/water azeotrope is removed. The azeotrope of isobutanol, ethanol and water is fed to a second distillation column from which an ethanol/water azeotrope is removed as an overhead stream. A stream comprising isobutanol, water and some ethanol is then cooled and fed to a decanter to form an isobutanol-rich phase and a water-rich phase. The isobutanol-rich phase is fed to a third distillation column to separate an isobutanol/water stream from an ethanol/water stream. The isobutanol/water stream can be used for the process of the invention.

Pervaporation

Generally, there are two steps involved in the removal of volatile components by pervaporation. One is the sorption of the volatile component into the membrane, and the other is the diffusion of the volatile component through the membrane due to a concentration gradient. The concentration gradient is created either by a vacuum applied to the opposite side of the membrane or through the use of a sweep gas, such as air or carbon dioxide, also applied along the backside of the membrane. Pervaporation for the separation of 1-butanol from a fermentation broth has been described by Meagher, M. M., et al in U.S. Pat. No. 5,755,967 (Column 5, line 20 through Column 20, line 59) and by Liu, F., et al (Separation and Purification Technology (2005) 42:273-282). According to U.S. Pat. No. 5,755,967, acetone and/or 1-butanol were selectively removed from an ABE fermentation broth using a pervaporation membrane comprising silicalite particles embedded in a polymer matrix. Examples of polymers include polydimethylsiloxane and cellulose acetate, and vacuum was used as the means to create the concentration gradient. The method of U.S. Pat. No. 5,755,967 can similarly be used to recover a stream comprising isobutanol and water from fermentation broth, and this stream can be used directly as the reactant of the present invention, or can be further treated by distillation to produce an aqueous isobutanol stream that can be used as the reactant of the present invention.

Gas Stripping

In general, gas stripping refers to the removal of volatile compounds, such as butanol, from fermentation broth by passing a flow of stripping gas, such as carbon dioxide, helium, hydrogen, nitrogen, or mixtures thereof, through the fermentor culture or through an external stripping column to form an enriched stripping gas. Gas stripping to remove 1-butanol from an ABE fermentation has been exemplified by Ezeji, T., et al (U.S. Patent Application No. 2005/0089979, paragraphs 16 through 84). According to U.S. 2005/0089979, a stripping gas (carbon dioxide and hydrogen) was fed into a fermentor via a sparger. The flow rate of the stripping gas through the fermentor was controlled to give the desired level of solvent removal. The flow rate of the stripping gas is dependent on such factors as configuration of the system, cell concentration and solvent concentration in the fermentor. This process can also be used to produce an enriched stripping gas comprising isobutanol and water, and this stream can be used directly as the reactant of the present invention, or can be further treated by distillation to produce an aqueous isobutanol stream that can be used as the reactant of the present invention.

Adsorption

Using adsorption, organic compounds of interest are removed from dilute aqueous solutions by selective sorption of the organic compound by a sorbant, such as a resin. Feldman, J. in U.S. Pat. No. 4,450,294 (Column 3, line 45 through Column 9, line 40 (Example 6)) describes the recovery of an oxygenated organic compound from a dilute aqueous solution with a cross-linked polyvinylpyridine resin or nuclear substituted derivative thereof. Suitable oxygenated organic compounds included ethanol, acetone, acetic acid, butyric acid, n-propanol and n-butanol. The adsorbed compound was desorbed using a hot inert gas such as carbon dioxide. This process can also be used to recover an aqueous stream comprising desorbed isobutanol, and this stream can be used directly as the reactant of the present invention, or can be further treated by distillation to produce an aqueous isobutanol stream that can be used as the reactant of the present invention.

Liquid-Liquid Extraction

Liquid-liquid extraction is a mass transfer operation in which a liquid solution (the feed) is contacted with an immiscible or nearly immiscible liquid (solvent) that exhibits preferential affinity or selectivity towards one or more of the components in the feed, allowing selective separation of said one or more components from the feed. The solvent comprising the one or more feed components can then be separated, if necessary, from the components by standard techniques, such as distillation or evaporation. One example of the use of liquid-liquid extraction for the separation of butyric acid and butanol from microbial fermentation broth has been described by Cenedella, R. J. in U.S. Pat. No. 4,628,116 (Column 2, line 28 through Column 8, line 57). According to U.S. Pat. No. 4,628,116, fermentation broth containing butyric acid and/or butanol was acidified to a pH from about 4 to about 3.5, and the acidified fermentation broth was then introduced into the bottom of a series of extraction columns containing vinyl bromide as the solvent. The aqueous fermentation broth, being less dense than the vinyl bromide, floated to the top of the column and was drawn off. Any butyric acid and/or butanol present in the fermentation broth was extracted into the vinyl bromide in the column. The column was then drawn down, the vinyl bromide was evaporated, resulting in purified butyric acid and/or butanol.

Other solvent systems for liquid-liquid extraction, such as decanol, have been described by Roffler, S. R., et al. (Bioprocess Eng. (1987) 1:1-12) and Taya, M., et al (J. Ferment. Technol. (1985) 63:181). In these systems, two phases were formed after the extraction: an upper less dense phase comprising decanol, 1-butanol and water, and a more dense phase comprising mainly decanol and water. Aqueous 1-butanol was recovered from the less dense phase by distillation.

These processes can also be used to obtain an aqueous stream comprising isobutanol that can be used directly as the reactant of the present invention, or can be further treated by distillation to produce an aqueous isobutanol stream that can be used as the reactant of the present invention.

Aqueous streams comprising isobutanol, as obtained by any of the methods above, can be the reactant for the process of the present invention. The reaction to form at least one isooctene is performed at a temperature of from about 50 degrees Centigrade to about 450 degrees Centigrade. In a more specific embodiment, the temperature is from about 100 degrees Centigrade to about 250 degrees Centigrade.

The reaction can be carried out under an inert atmosphere at a pressure of from about atmospheric pressure (about 0.1 MPa) to about 20.7 MPa. In a more specific embodiment, the pressure is from about 0.1 MPa to about 3.45 MPa. Suitable inert gases include nitrogen, argon and helium.

The reaction can be carried out in liquid or vapor phase and can be run in either batch or continuous mode as described, for example, in H. Scott Fogler, (*Elements of Chemical Reaction Engineering*, 2$^{nd}$ Edition, (1992) Prentice-Hall Inc, CA).

The at least one acid catalyst can be a homogeneous or heterogeneous catalyst. Homogeneous catalysis is catalysis in which all reactants and the catalyst are molecularly dispersed in one phase. Homogeneous acid catalysts include, but are not limited to, inorganic acids, organic sulfonic acids, heteropolyacids, fluoroalkyl sulfonic acids, metal sulfonates, metal trifluoroacetates, compounds thereof and combinations thereof. Examples of homogeneous acid catalysts include sulfuric acid, fluorosulfonic acid, phosphoric acid, p-toluenesulfonic acid, benzenesulfonic acid, hydrogen fluoride, phosphotungstic acid, phosphomolybdic acid, and trifluoromethanesulfonic acid.

Heterogeneous catalysis refers to catalysis in which the catalyst constitutes a separate phase from the reactants and products. Heterogeneous acid catalysts include, but are not limited to 1) heterogeneous heteropolyacids (HPAs), 2) natural clay minerals, such as those containing alumina or silica, 3) cation exchange resins, 4) metal oxides, 5) mixed metal oxides, 6) metal salts such as metal sulfides, metal sulfates, metal sulfonates, metal nitrates, metal phosphates, metal phosphonates, metal molybdates, metal tungstates, metal borates, 7) zeolites, and 8) combinations of groups 1-7. See, for example, Solid Acid and Base Catalysts, pages 231-273 (Tanabe, K., in Catalysis: Science and Technology, Anderson, J. and Boudart, M (eds.) 1981 Springer-Verlag, New York) for a description of solid catalysts.

The heterogeneous acid catalyst may also be supported on a catalyst support. A support is a material on which the acid catalyst is dispersed. Catalyst supports are well known in the art and are described, for example, in Satterfield, C. N. (Heterogeneous Catalysis in Industrial Practice, 2$^{nd}$ Edition, Chapter 4 (1991) McGraw-Hill, New York).

In one embodiment of the invention, the reaction is carried out using a heterogeneous catalyst, and the temperature and pressure are chosen so as to maintain the reactant and reaction product in the vapor phase. In a more specific embodiment, the reactant is obtained from a fermentation broth that is subjected to distillation to produce a vapor phase having at least about 33% water. The vapor phase is directly used as a reactant in a vapor phase reaction in which the acid catalyst is a heterogeneous catalyst, and the temperature and pressure are chosen so as to maintain the reactant and reaction product in the vapor phase. It is believed that this vapor phase reaction would be economically desirable because the vapor phase is not first cooled to a liquid prior to performing the reaction.

One skilled in the art will know that conditions, such as temperature, catalytic metal, support, reactor configuration and time can affect the reaction kinetics, product yield and product selectivity. Depending on the reaction conditions, such as the particular catalyst used, products other than isooctenes may be produced when isobutanol is contacted with an acid catalyst. Additional products comprise dibutyl ethers (such as di-1-butyl ether) and butenes. Standard experimentation, performed as described in the Examples herein, can be used to optimize the yield of isooctenes from the reaction.

Following the reaction, if necessary, the catalyst can be separated from the reaction product by any suitable technique known to those skilled in the art, such as decantation, filtration, extraction or membrane separation (see Perry, R. H. and Green, D. W. (eds), Perry's Chemical Engineer's Handbook, 7$^{th}$ Edition, Section 13, 1997, McGraw-Hill, New York, Sections 18 and 22).

The at least one isooctene can be recovered from the reaction product by distillation as described in Seader, J. D., et al (Distillation, in Perry, R. H. and Green, D. W. (eds), Perry's Chemical Engineer's Handbook, 7$^{th}$ Edition, Section 13, 1997, McGraw-Hill, New York). Alternatively, the at least one isooctene can be recovered by phase separation, or extraction with a suitable solvent, such as trimethylpentane or octane, as is well known in the art. Unreacted isobutanol can be recovered following separation of the at least one isooctene and used in subsequent reactions.

The present process and certain embodiments for accomplishing it are shown in greater detail in the Drawing figures.

Referring now to FIG. 1, there is shown a block diagram illustrating in a very general way apparatus 10 for deriving isooctenes from aqueous isobutanol produced by fermentation. An aqueous stream 12 of biomass-derived carbohydrates is introduced into a fermentor 14. The fermentor 14 contains at least one microorganism (not shown) capable of fermenting the carbohydrates to produce a fermentation broth that comprises isobutanol and water. A stream 16 of the fermentation broth is introduced into refining apparatus 18 in order to make a stream of aqueous isobutanol. The aqueous isobutanol is removed from the refining apparatus 18 as stream 20. Some water is removed from the refining apparatus 18 as stream 22. Other organic components present in the fermentation broth may be removed as stream 24. The aqueous isobutanol stream 20 is introduced into reaction vessel 26 containing an acid catalyst (not shown) capable of converting the isobutanol into a reaction product comprising at least one isooctene. The reaction product is removed as stream 28.

Figure 2:
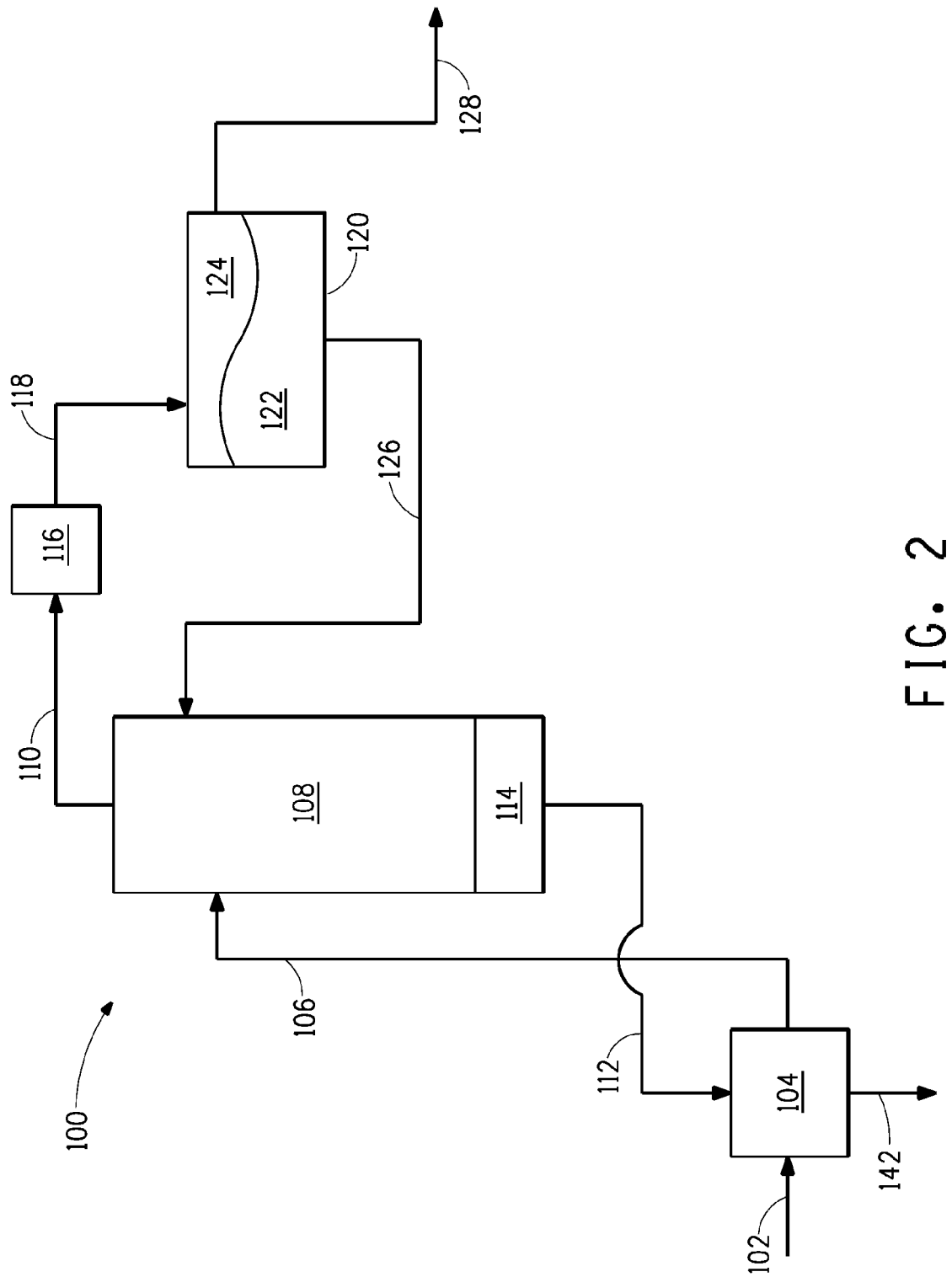
FIG. 2 illustrates a method for producing an isobutanol/water stream using distillation wherein fermentation broth comprising isobutanol, but being substantially free of acetone and ethanol, is used as the feed stream.

Referring now to FIG. 2, there is shown a block diagram for refining apparatus 100, suitable for producing an aqueous isobutanol stream, when the fermentation broth comprises isobutanol and water, and is substantially free of ethanol. A stream 102 of fermentation broth is introduced into a feed preheater 104 to raise the broth to a temperature of approximately 95° C. to produce a heated feed stream 106 which is introduced into a beer column 108. The design of the beer column 108 needs to have a sufficient number of theoretical stages to cause separation of isobutanol from water such that an isobutanol/water azeotrope can be removed as a vaporous isobutanol/water azeotrope overhead stream 110 and hot water as a bottoms stream 112. Bottoms stream 112, is used to supply heat to feed preheater 104 and leaves feed preheater 104 as a lower temperature bottoms stream 142. Reboiler 114 is used to supply heat to beer column 108. Vaporous isobutanol/water azeotrope overhead stream 110 is roughly 67% by weight isobutanol of the total isobutanol and water stream. This is the first opportunity by which a concentrated and partially purified isobutanol and water stream could be obtained; this partially purified isobutanol and water stream can be used as the feed stream to a reaction vessel (not shown) in which the aqueous isobutanol is catalytically converted to a reaction product that comprises at least one isooctene. Vaporous isobutanol/water azeotrope stream 110 can be fed to a condenser 116, which lowers the stream temperature causing the vaporous isobutanol/water azeotrope overhead stream 110 to condense into a biphasic liquid stream 118, which is introduced into decanter 120. Decanter 120 will contain a lower phase 122 that is approximately 94% by weight water and approximately 6% by weight isobutanol and an upper phase 124 that is around 80% by weight isobutanol and 20% by weight water. A reflux stream 126 of lower phase 122 is introduced near the top of beer column 108. A stream 128 of upper phase 124 can then be used as the feed stream to a reaction vessel (not shown) in which the aqueous isobutanol is catalytically converted to a reaction product that comprises at least one isooctene.

Figure 3:
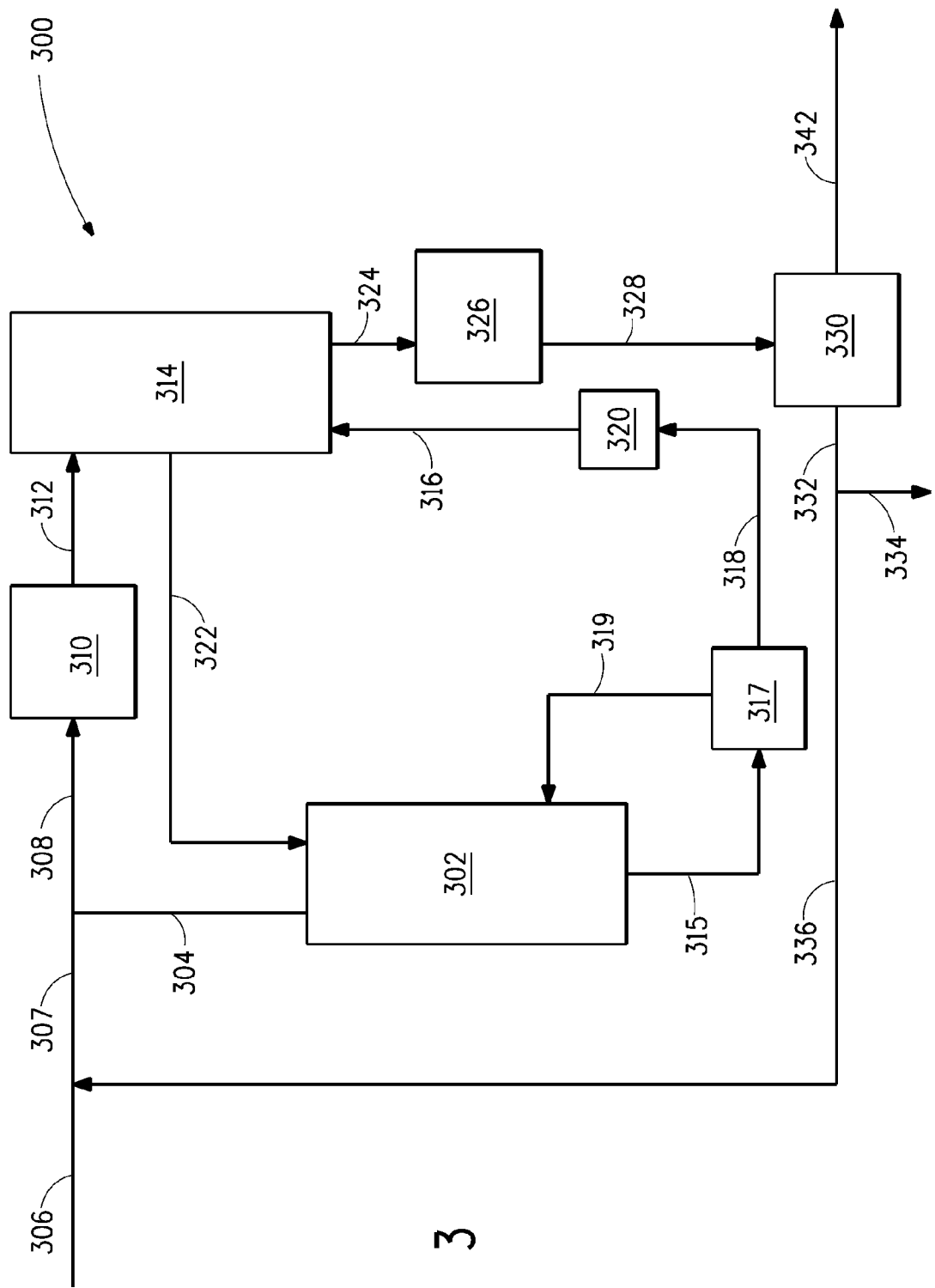
FIG. 3 illustrates a method for producing an isobutanol/water stream using gas stripping wherein fermentation broth comprising isobutanol and water is used as the feed stream.

Referring now to FIG. 3, there is shown a block diagram for refining apparatus 300, suitable for producing an aqueous isobutanol stream when the fermentation broth comprises isobutanol and water, and may additionally comprise ethanol. Fermentor 302 contains a fermentation broth comprising liquid isobutanol and water and a gas phase comprising $CO_2$ and to a lesser extent some vaporous isobutanol and water. Both phases may additionally comprise ethanol. A $CO_2$ stream 304 is then mixed with combined $CO_2$ stream 307 to give second combined $CO_2$ stream 308. Second combined $CO_2$ stream 308 is then fed to heater 310 and heated to 60° C. to give heated $CO_2$ stream 312. Heated $CO_2$ stream is then fed to gas stripping column 314 where it is brought into contact with heated clarified fermentation broth stream 316. Heated clarified fermentation broth stream 316 is obtained as a clarified fermentation broth stream 318 from cell separator 317 and heated to 50° C. in heater 320. Clarified fermentation broth stream 318 is obtained following separation of cells in cell separator 317. Also leaving cell separator 317 is concentrated cell stream 319 which is recycled directly to fermentor 302. The feed stream 315 to cell separator 317 comprises the liquid phase of fermentor 302. Gas stripping column 314 contains a sufficient number of theoretical stages necessary to effect the transfer of isobutanol from the liquid phase to the gas phase. The number of theoretical stages is dependent on the contents of both streams 312 and 316, as well as their flow rates and temperatures. Leaving gas stripping column 314 is an isobutanol depleted clarified fermentation broth stream 322 that is recirculated to fermentor 302. An isobutanol enriched gas stream 324 leaving gas stripping column 314 is then fed to compressor 326. Following compression, a compressed gas stream comprising isobutanol 328 is then fed to condenser 330 where the isobutanol in the gas stream is condensed into a liquid phase that is separate from non-condensable components in the stream 328. Leaving the condenser 330 is isobutanol depleted gas stream 332. A first portion of gas stream 332 is bled from the system as bleed gas stream 334, and the remaining second portion of isobutanol depleted gas stream 332, stream 336, is then mixed with makeup $CO_2$ gas stream 306 to form combined $CO_2$ gas stream 307. The condensed isobutanol phase in condenser 330 leaves as aqueous isobutanol stream 342 and can be used as the feed to a distillation apparatus that is capable of separating aqueous isobutanol from ethanol, or can be used directly as a feed to a reaction vessel (not shown) in which the aqueous isobutanol is catalytically converted to a reaction product that comprises at least one isooctene.

Figure 4:
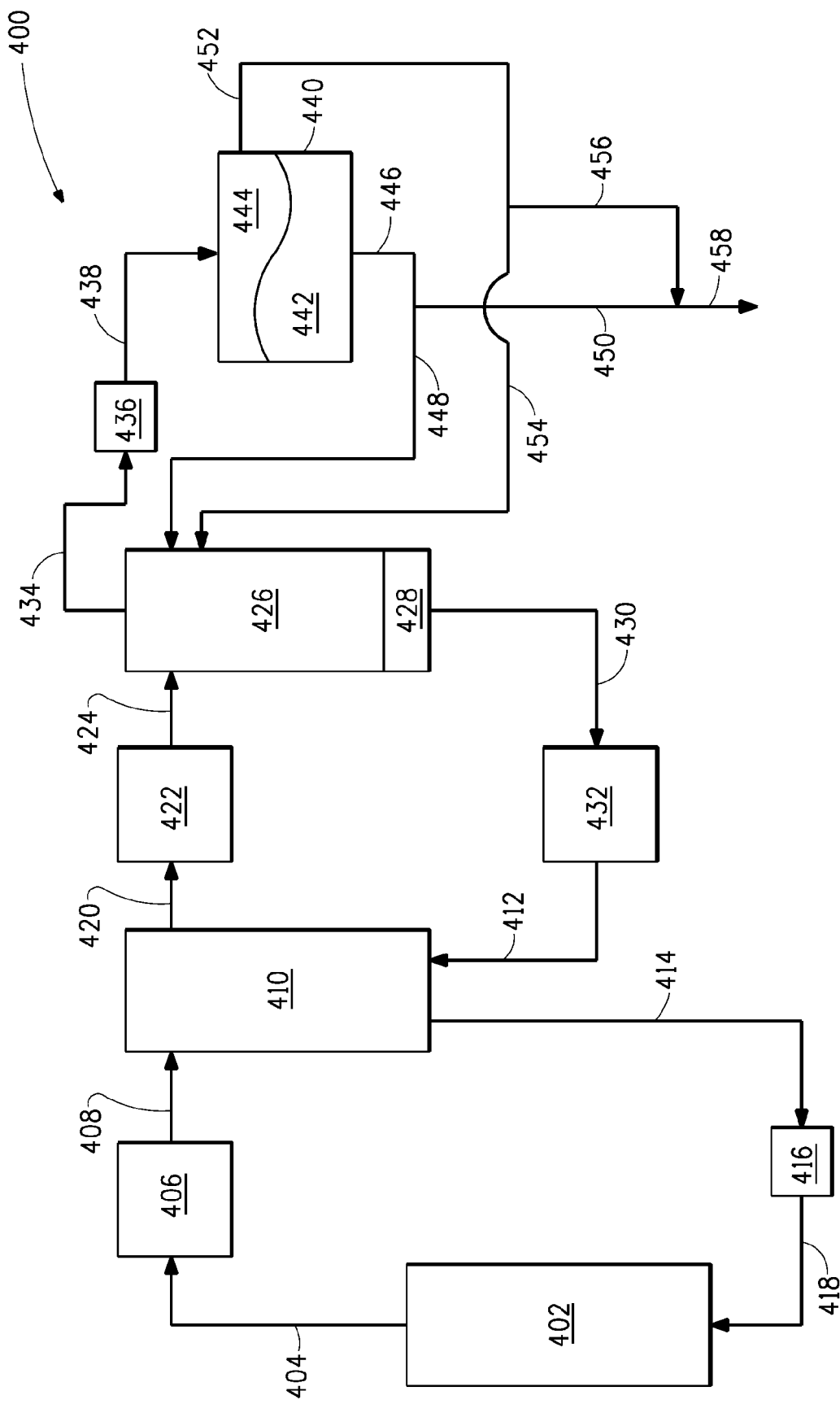
FIG. 4 illustrates a method for producing an isobutanol/water stream using liquid-liquid extraction wherein fermentation broth comprising isobutanol and water is used as the feed stream.

Referring now to FIG. 4, there is shown a block diagram for refining apparatus 400, suitable for producing an aqueous isobutanol stream, when the fermentation broth comprises isobutanol and water, and may additionally comprise ethanol. Fermentor 402 contains a fermentation broth comprising isobutanol and water and a gas phase comprising $CO_2$ and to a lesser extent some vaporous isobutanol and water. Both phases may additionally comprise ethanol. A stream 404 of fermentation broth is introduced into a feed preheater 406 to raise the broth temperature to produce a heated fermentation broth stream 408 which is introduced into solvent extractor 410. In solvent extractor 410, heated fermentation broth stream 408 is brought into contact with cooled solvent stream 412, the solvent used in this case being decanol. Leaving solvent extractor 410, is raffinate stream 414 that is depleted in isobutanol. Raffinate stream 414 is introduced into raffinate cooler 416 where it is lowered in temperature and returned to fermentor 402 as cooled raffinate stream 418. Also leaving solvent extractor 410 is extract stream 420 that contains solvent, isobutanol and water. Extract stream 420 is introduced into solvent heater 422 where it is heated. Heated extract stream 424 is then introduced into solvent recovery distillation column 426 where the solvent is caused to separate from the isobutanol and water. Solvent column 426 is equipped with reboiler 428 necessary to supply heat to solvent column 426. Leaving the bottom of solvent column 426 is solvent stream 430. Solvent stream 430 is then introduced into solvent cooler 432 where it is cooled to 50° C. Cooled solvent stream 412 leaves solvent cooler 432 and is returned to extractor 410. Leaving the top of solvent column 426 is solvent overhead stream 434 that contains an azeotropic mixture of isobutanol and water with trace amounts of solvent. This represents the first substantially concentrated and partially purified isobutanol/water stream that could fed to a reaction vessel (not shown) for catalytically converting the isobutanol to a reaction product that comprises at least one isooctene. Optionally, solvent overhead stream 434 could be fed into condenser 436 where the vaporous solvent overhead stream is caused to condense into a biphasic liquid stream 438 and introduced into decanter 440. Decanter 440 will contain a lower phase 442 that is approximately 94% by weight water and approximately 6% by weight isobutanol and an upper phase 444 that is around 80% by weight isobutanol and 20% by weight water and a small amount of solvent. The lower phase 442 of decanter 440 leaves decanter 440 as water rich stream 446. Water rich stream 446 is then split into two fractions. A first fraction of water rich stream 446 is returned as water rich reflux stream 448 to solvent column 426. A second fraction of water rich stream 446, water rich product stream 450, is sent on to be mixed with isobutanol rich stream 456. A stream 452 of upper phase 444 is split into two streams. Stream 454 is fed to solvent column 426 to be used as reflux. Stream 456 is combined with stream 450 to produce product stream 458. Product stream 458 can be introduced as the feed to a distillation apparatus that is capable of separating aqueous isobutanol from ethanol or can be used directly as a feed to a reaction vessel (not shown) in which the aqueous isobutanol is catalytically converted to a reaction product that comprises at least one isooctene.

Figure 5:
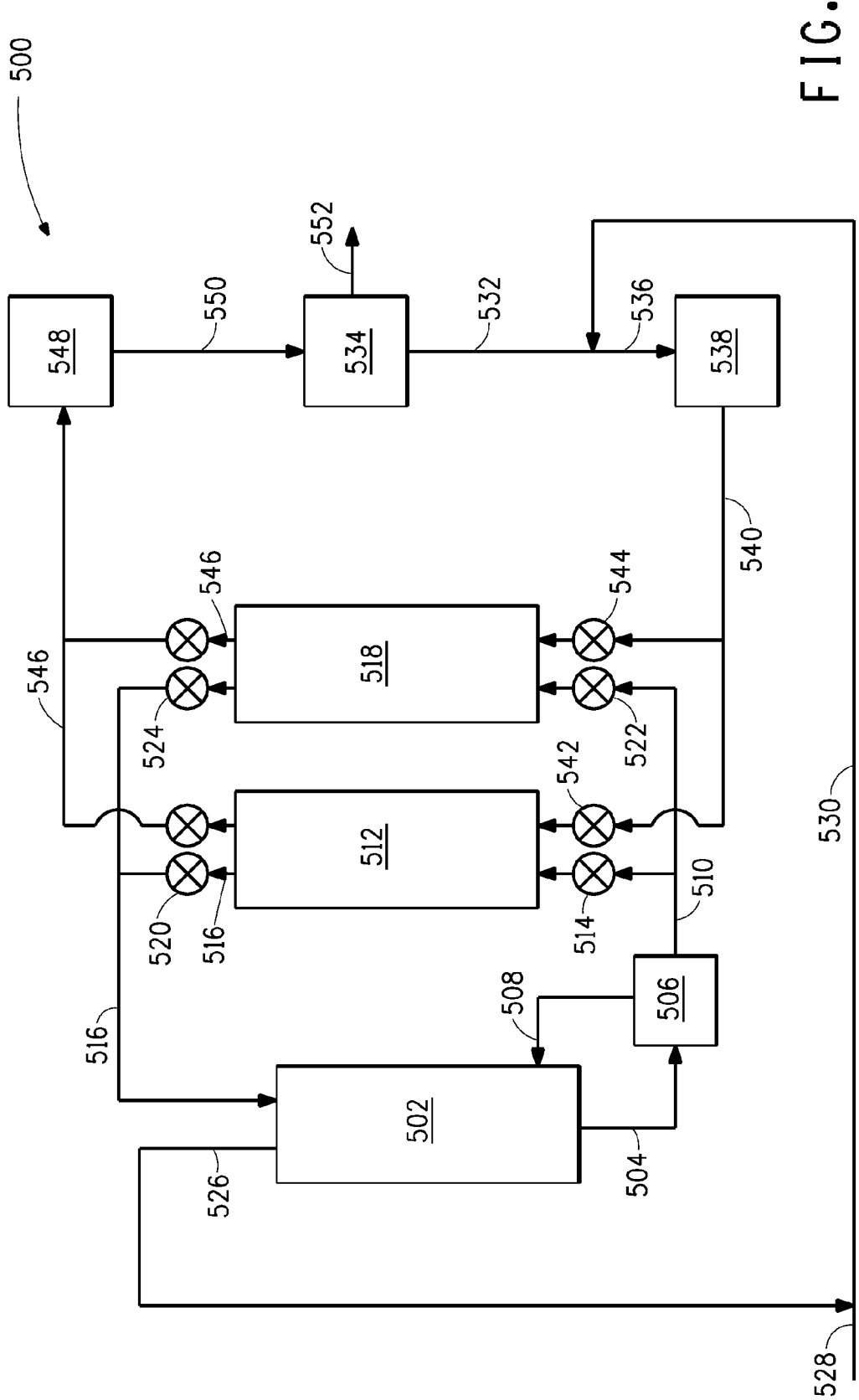
FIG. 5 illustrates a method for producing an isobutanol/water stream using adsorption wherein fermentation broth comprising isobutanol and water is used as the feed stream.

Referring now to FIG. 5, there is shown a block diagram for refining apparatus 500, suitable for concentrating isobutanol, when the fermentation broth comprises isobutanol and water, and may additionally comprise ethanol. Fermentor 502 contains a fermentation broth comprising isobutanol and water and a gas phase comprising $CO_2$ and to a lesser extent some vaporous isobutanol and water. Both phases may additionally comprise ethanol. An isobutanol-containing fermentation broth stream 504 leaving fermentor 502 is introduced into cell separator 506. Cell separator 506 can be comprised of centrifuges or membrane units to accomplish the separation of cells from the fermentation broth. Leaving cell separator 506 is cell-containing stream 508 which is recycled back to fermentor 502. Also leaving cell separator 506 is clarified fermentation broth stream 510. Clarified fermentation broth stream 510 is then introduced into one or a series of adsorption columns 512 where the isobutanol is preferentially removed from the liquid stream and adsorbed on the solid phase adsorbent (not shown). Diagrammatically, this is shown in FIG. 5 as a two adsorption column system, although more or fewer columns could be used. The flow of clarified fermentation broth stream 510 is directed to the appropriate adsorption column 512 through the use of switching valve 514. Leaving the top of adsorption column 512 is isobutanol depleted stream 516 which passes through switching valve 520 and is returned to fermentor 502. When adsorption column 512 reaches capacity, as evidenced by an increase in the isobutanol concentration of the isobutanol depleted stream 516, flow of clarified fermentation broth stream 510 is then directed through switching valve 522 by closing switching valve 514. This causes the flow of clarified fermentation broth stream 510 to enter second adsorption column 518 where the isobutanol is adsorbed onto the adsorbent (not shown). Leaving the top of second adsorption column 518 is an isobutanol depleted stream which is essentially the same as isobutanol depleted stream 516. Switching valves 520 and 524 perform the function to divert flow of depleted isobutanol stream 516 from returning to one of the other columns that is currently being desorbed. When either adsorption column 512 or second adsorption column 518 reaches capacity, the isobutanol and water adsorbed into the pores of the adsorbent must be removed. This is accomplished using a heated gas stream to effect desorption of adsorbed isobutanol and water. The $CO_2$ stream 526 leaving fermentor 502 is first mixed with makeup gas stream 528 to produced combined gas stream 530. Combined gas stream 530 is then mixed with the cooled gas stream 532 leaving decanter 534 to form second combined gas stream 536. Second combined gas stream 536 is then fed to heater 538. Leaving heater 538 is heated gas stream 540 which is diverted into one of the two adsorption columns through the control of switching valves 542 and 544. When passed through either adsorption column 512 or second adsorption column 518, heated gas stream 540 removes the isobutanol and water from the solid adsorbent. Leaving either adsorption column is isobutanol/water rich gas stream 546. Isobutanol/water rich gas stream 546 then enters gas chiller 548 which causes the vaporous isobutanol and water in isobutanol/water rich gas stream 546 to condense into a liquid phase that is separate from the other noncondensable species in the stream. Leaving gas chiller 548 is a biphasic gas stream 550 which is fed into decanter 534. In decanter 534 the condensed isobutanol/water phase is separated from the gas stream. Leaving decanter 534 is an aqueous isobutanol stream 552 which is then fed to a distillation apparatus that is capable of separating aqueous isobutanol from ethanol, or used directly as a feed to a reaction vessel (not shown) in which the aqueous isobutanol is catalytically converted to a reaction product that comprises at least one isooctene. Also leaving decanter 534 is cooled gas stream 532.

Figure 6:
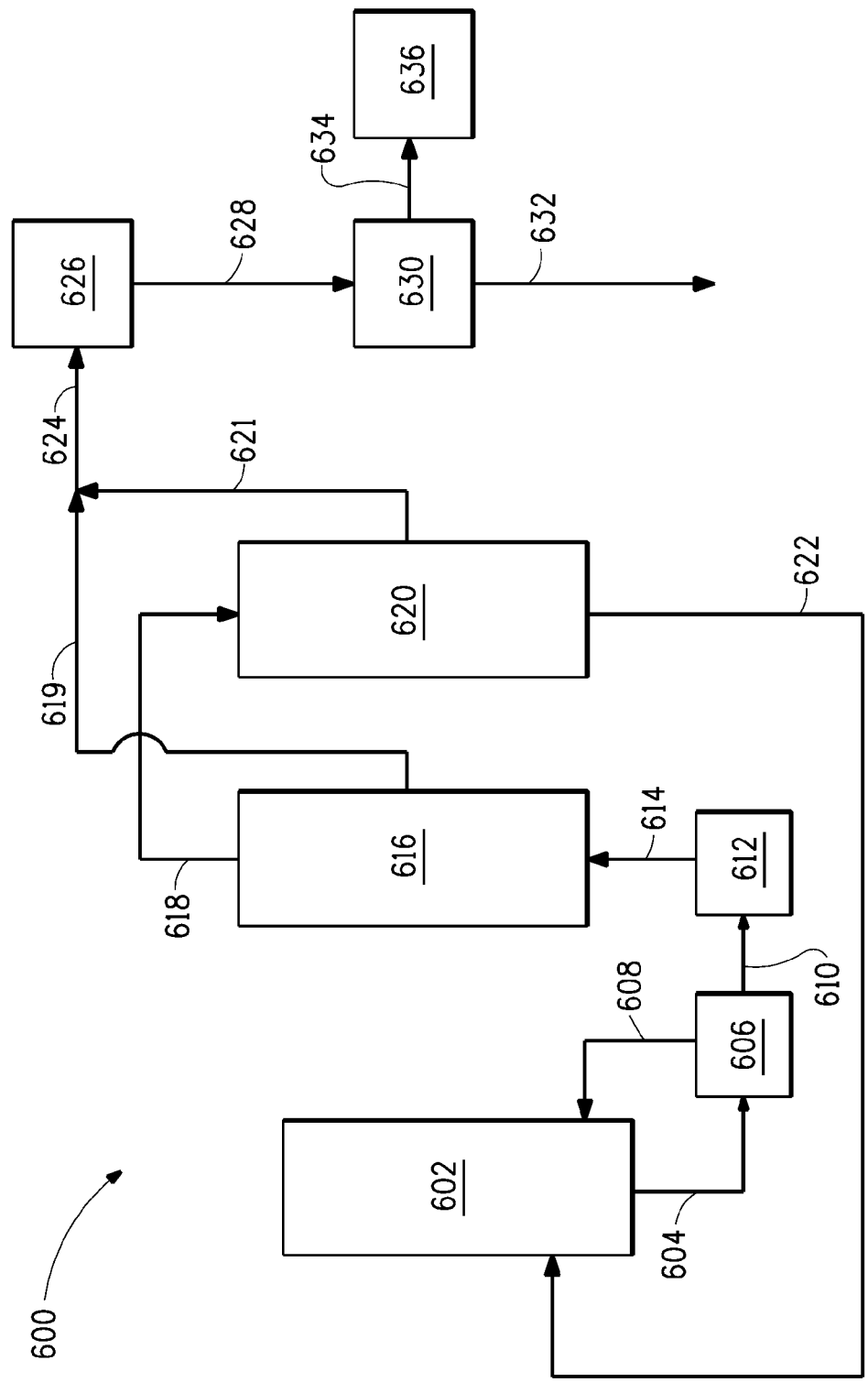
FIG. 6 illustrates a method for producing an isobutanol/water stream using pervaporation wherein fermentation broth comprising isobutanol and water is used as the feed stream.

Referring now to FIG. 6, there is shown a block diagram for refining apparatus 600, suitable for producing an aqueous isobutanol stream, when the fermentation broth comprises isobutanol and water, and may additionally comprise ethanol. Fermentor 602 contains a fermentation broth comprising isobutanol and water and a gas phase comprising $CO_2$ and to a lesser extent some vaporous isobutanol and water. Both phases may additionally comprise ethanol. An isobutanol-containing fermentation broth stream 604 leaving fermentor 602 is introduced into cell separator 606. Isobutanol-containing stream 604 may contain some non-condensable gas species, such as carbon dioxide. Cell separator 606 can be comprised of centrifuges or membrane units to accomplish the separation of cells from the fermentation broth. Leaving cell separator 606 is concentrated cell stream 608 that is recycled back to fermentor 602. Also leaving cell separator 606 is clarified fermentation broth stream 610. Clarified fermentation broth stream 610 can then be introduced into optional heater 612 where it is optionally raised to a temperature of 40 to 80° C. Leaving optional heater 612 is optionally heated clarified broth stream 614. Optionally heated clarified broth stream 614 is then introduced to the liquid side of first pervaporation module 616. First pervaporation module 616 contains a liquid side that is separated from a low pressure or gas phase side by a membrane (not shown). The membrane serves to keep the phases separated and also exhibits a certain affinity for isobutanol. In the process of pervaporation any number of pervaporation modules can used to effect the separation. The number is determined by the concentration of species to be removed and the size of the streams to be processed. Diagrammatically, two pervaporation units are shown in FIG. 6, although any number of units can be used. In first pervaporation module 616 isobutanol is selectively removed from the liquid phase through a concentration gradient caused when a vacuum is applied to the low pressure side of the membrane. Optionally a sweep gas can be applied to the non-liquid side of the membrane to accomplish a similar purpose. The first depleted isobutanol stream 618 exiting first pervaporation module 616 then enters second pervaporation module 620. Second isobutanol depleted stream 622 exiting second pervaporation module 620 is then recycled back to fermentor 602. The low pressure streams 619, 621 exiting first and second pervaporation modules 616 and 620, respectively, are combined to form low pressure isobutanol/water stream 624. Low pressure isobutanol stream/water 624 is then fed into cooler 626 where the isobutanol and water in low pressure isobutanol/water stream 624 is caused to condense. Leaving cooler 626 is condensed low pressure isobutanol/water stream 628. Condensed low pressure isobutanol/water stream 628 is then fed to receiver vessel 630 where the condensed isobutanol/water stream collects and is withdrawn as stream 632. Vacuum pump 636 is connected to the receiving vessel 630 by a connector 634, thereby supplying vacuum to apparatus 600. Non-condensable gas stream 634 exits decanter 630 and is fed to vacuum pump 636. Aqueous isobutanol stream 632 is then fed to a distillation apparatus that is capable of separating aqueous isobutanol from ethanol, or is used directly as a feed to a reaction vessel (not shown) in which the aqueous isobutanol is catalytically converted to a reaction product that comprises at least one isooctene.

Figure 7:
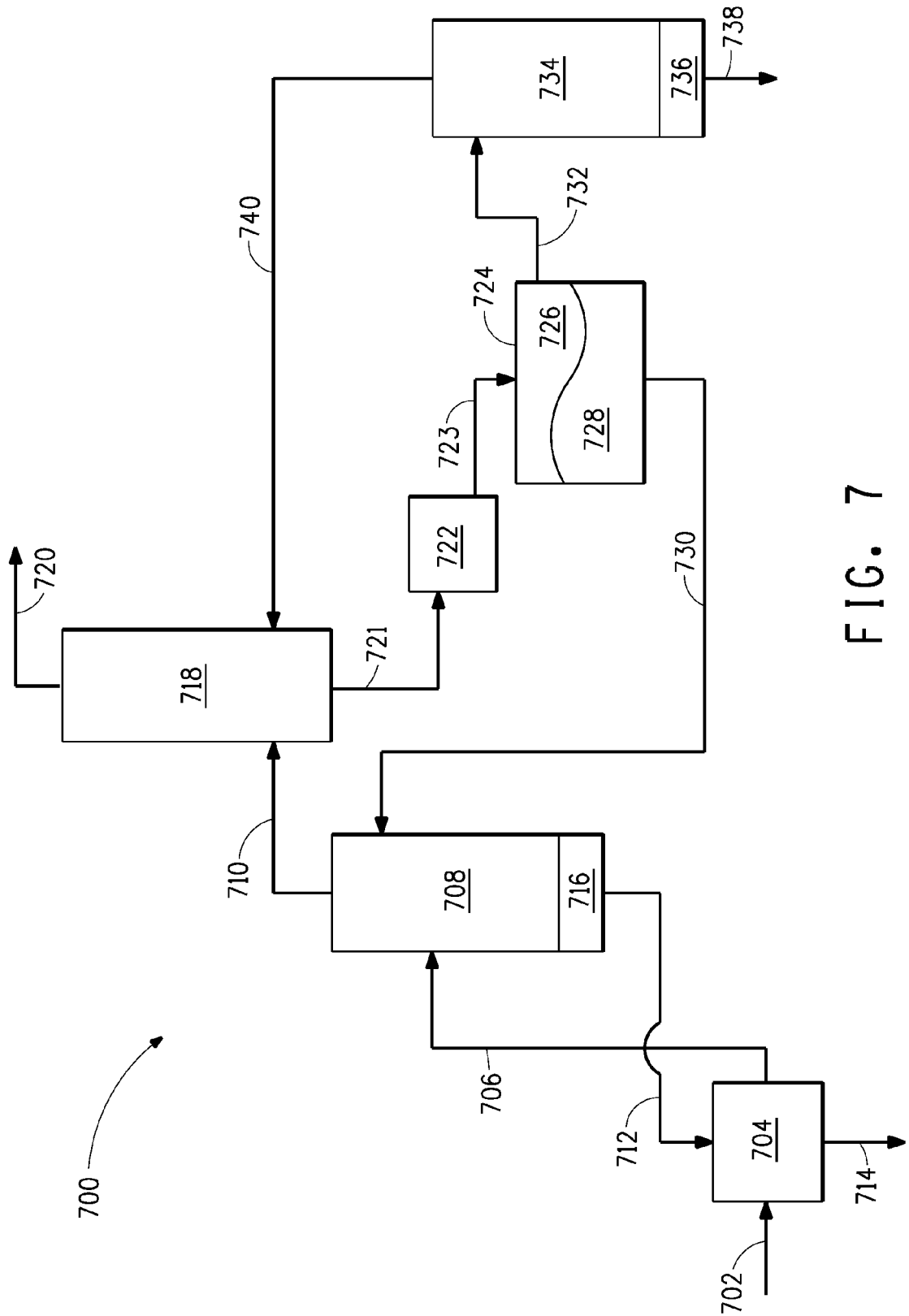
FIG. 7 illustrates a method for producing an isobutanol/water stream using distillation wherein fermentation broth comprising isobutanol and ethanol, but being substantially free of acetone, is used as the feed stream.

Referring now to FIG. 7, there is shown a block diagram for refining apparatus 700, suitable for producing an aqueous isobutanol stream, when the fermentation broth comprises isobutanol, ethanol, and water. A stream 702 of fermentation broth is introduced into a feed preheater 704 to raise the broth temperature to produce a heated feed stream 706 which is introduced into a beer column 708. The beer column 708 needs to have a sufficient number of theoretical stages to cause separation of a ternary azeotrope of isobutanol, ethanol, and water to be removed as an overhead product stream 710 and a hot water bottoms stream 712. Hot water bottoms stream 712, is used to supply heat to feed preheater 704 and leaves as lower temperature bottoms stream 714. Reboiler 716 is used to supply heat to beer column 708. Overhead stream 710 is a ternary azeotrope of isobutanol, ethanol and water and is fed to ethanol column 718. Ethanol column 718 contains a sufficient number of theoretical stages to effect the separation of an ethanol water azeotrope as overhead stream 720 and biphasic bottoms stream 721 comprising isobutanol, ethanol and water. Biphasic bottoms stream 721 is then fed to cooler 722 where the temperature is lowered to ensure complete phase separation. Leaving cooler 722 is cooled bottoms stream 723 which is then introduced into decanter 724 where an isobutanol rich phase 726 is allowed to phase separate from a water rich phase 728. Both phases still contain some amount of ethanol. A water rich phase stream 730 comprising a small amount of ethanol and isobutanol is returned to beer column 708. An isobutanol rich stream 732 comprising a small amount of water and ethanol is fed to isobutanol column 734. Isobutanol column 734 is equipped with reboiler 736 necessary to supply heat to the column. Isobutanol column 734 is equipped with a sufficient amount of theoretical stages to produce a isobutanol/water bottoms stream 738 and an ethanol/water azeotropic stream 740 that is returned to ethanol column 718. Isobutanol/water bottoms stream 738 (i.e., aqueous isobutanol stream) can then be used as a feed to a reaction vessel (not shown) in which the aqueous isobutanol is catalytically converted to a reaction product that comprises at least one isooctene.

The at least one recovered isooctene can be further converted to isooctanes, isooctanols or isooctyl alkyl ethers, which are useful fuel additives. The terms isooctanes and isooctanols are meant to denote eight-carbon compounds having at least one secondary or tertiary carbon. The term isooctyl alkyl ether is meant to denote a compound, the isooctyl moiety of which contains eight carbons, at least one carbon of which is a secondary or tertiary carbon.

In one embodiment of the invention, the at least one isooctene is contacted with at least one hydrogenation catalyst in the presence of hydrogen to produce a reaction product comprising at least one isooctane. Suitable solvents, catalysts, apparatus, and procedures for hydrogenation in general can be found in Augustine, R. L. (Heterogeneous Catalysis for the Synthetic Chemist, Marcel Decker, New York, 1996, Section 3); the hydrogenation can be performed as exemplified in U.S. Patent Application No. 2005/0054861, paragraphs 17-36). In general, the reaction is performed at a temperature of from about 50 degrees Centigrade to about 300 degrees Centigrade, and at a pressure of from about 0.1 MPa to about 20 MPa. The principal component of the hydrogenation catalyst may be selected from metals from the group consisting of palladium, ruthenium, rhenium, rhodium, iridium, platinum, nickel, cobalt, copper, iron, osmium; compounds thereof; and combinations thereof. The catalyst may be supported or unsupported. The at least one isooctane can be separated from the hydrogenation catalyst by any suitable method, including decantation. The at least one isooctane can then be recovered (for example, if the reaction does not go to completion or if a homogeneous catalyst is used) from the reaction product by distillation (see Seader, J. D., supra) to obtain a recovered isooctane, and added to a transportation fuel. Alternatively, the reaction product itself can be added to a transportation fuel. If present, unreacted isooctenes can be used in subsequent reactions to produce isooctanes.

In another embodiment, the at least one isooctene is contacted with water in the presence of at least one acidic catalyst to produce a reaction product comprising at least one isooctanol. The hydration of olefins is well known, and a method to carry out the hydration using a zeolite catalyst is described in U.S. Pat. No. 5,288,924 (Column 3, line 48 to Column 7, line 66), wherein a temperature of from about 60 degrees Centigrade to about 450 degrees Centigrade and a pressure of from about 700 kPa to about 24,500 kPa are used. The water to olefin ratio is from about 0.05 to about 30. Where a solid acid catalyst is used, such as a zeolite, the at least one isooctanol can be separated from the at least one acid catalyst by any suitable method, including decantation. The at least one isooctanol can then be recovered from the reaction product by distillation (see Seader, J. D., supra) to obtain a recovered isooctanol, and added to a transportation fuel. Alternatively, the reaction product itself can be added to a transportation fuel. Unreacted isooctenes, if present, can be used in subsequent reactions to produce isooctanols.

In still another embodiment, the at least one isooctene is contacted with at least one acid catalyst in the presence of at least one straight-chain or branched $C_1$ to $C_5$ alcohol to produce a reaction product comprising at least one isooctyl alkyl ether. One skilled in the art will recognize that $C_1$ and $C_2$ alcohols cannot be branched. The etherification reaction is described by Stüwe, A., et al (Synthesis of MTBE and TAME and related reactions, Section 3.11, in Handbook of Heterogeneous Catalysis, Volume 4, (Ertl, G., Knözinger, H., and Weitkamp, J. (eds), 1997, VCH Verlagsgesellschaft mbH, Weinheim, Germany)) for the production of methyl-t-butyl ether. The etherification reaction is generally carried out at temperature of from about 50 degrees Centigrade to about 200 degrees Centigrade at a pressure of from about 0.1 to about 20.7 MPa. Suitable acid catalysts include, but are not limited to, acidic ion exchange resins. Where a solid acid catalyst is used, such as an ion-exchange resin, the at least one isooctyl alkyl ether can be separated from the at least one acid catalyst by any suitable method, including decantation. The at least one isooctyl alkyl ether can then optionally be recovered from the reaction product by distillation (see Seader, J. D., supra) to obtain a recovered isooctyl alkyl ether, and added to a transportation fuel. If present, unreacted isooctenes can be used in subsequent reactions to produce isooctyl alkyl ethers.

According to embodiments described above, isooctenes produced by the reaction of aqueous isobutanol with at least one acid catalyst are first recovered from the reaction product prior to being converted to compounds useful in transportation fuels. However, as described in the following embodiments, the reaction product comprising isooctenes can also be used in subsequent reactions without first recovering said isooctenes.

Thus, one alternative embodiment of the invention is a process for making at least one isooctane comprising:

(a) contacting a reactant comprising isobutanol and at least about 5% water (by weight relative to the weight of the water plus isobutanol) with at least one acid catalyst at a temperature of about 50 degrees C. to about 450 degrees C. and a pressure from about 0.1 MPa to about 20.7 MPa to produce a first reaction product comprising at least one isooctene;

(b) contacting said first reaction product with hydrogen in the presence of at least one hydrogenation catalyst to produce a second reaction product comprising at least one isooctane; and (c) recovering the at least one isooctane from the second reaction product to produce a recovered isooctane.

The at least one recovered isooctane can then be added to a transportation fuel.

Another embodiment of the invention is a process for making at least one isooctanol comprising:

(a) contacting a reactant comprising isobutanol and at least about 5% water (by weight relative to the weight of the water plus isobutanol) with at least one acid catalyst at a temperature of about 50 degrees C. to about 450 degrees C. and a pressure from about 0.1 MPa to about 20.7 MPa to produce a first reaction product comprising at least one isooctene;

(c) contacting said first reaction product with water and at least one acid catalyst to produce a second reaction product comprising at least one isooctanol; and (d) optionally recovering the at least one isooctanol from the second reaction product to obtain at least one recovered isooctanol.

The third reaction product or the at least one recovered isooctane can then be added to a transportation fuel.

GENERAL METHODS AND MATERIALS

In the following examples, "C" is degrees Centigrade, "mg" is milligram; "ml" is milliliter; "MPa" is mega Pascal; "wt. %" is weight percent; "GC/MS" is gas chromatography/mass spectrometry.

Amberlyst® (manufactured by Rohm and Haas, Philadelphia, Pa.), isobutanol and $H_2SO_4$ were obtained from Alfa Aesar (Ward Hill, Mass.); CBV-3020E was obtained from PQ Corporation (Berwyn, Pa.); 13% Nafion®/$SiO_2$ can be obtained from Engelhard; and H-Mordenite can be obtained from Zeolyst Intl. (Valley Forge, Pa.).

General Procedure for the Conversion of Isobutanol to Isooctenes

A mixture of isobutanol, water, and catalyst was contained in a 2 ml vial equipped with a magnetic stir bar. The vial was sealed with a serum cap perforated with a needle to facilitate gas exchange. The vial was placed in a block heater enclosed in a pressure vessel. The vessel was purged with nitrogen and the pressure was set at 6.9 MPa. The block was brought to the indicated temperature and controlled at that temperature for the time indicated. After cooling and venting, the contents of the vial were analyzed by GC/MS using a capillary column (either (a) CP-Wax 58 [Varian; Palo Alto, Calif.], 25 m×0.25 mm, 45 C/6 min, 10 C/min up to 200 C, 200 C/10 min, or (b) DB-1701 [J&W (available through Agilent; Palo Alto, Calif.)], 30 m×0.25 mm, 50 C/10 min, 10 C/min up to 250 C, 250 C/2 min).

The examples below were performed according to this procedure under the conditions indicated for each example.

EXAMPLES 1-5

Reaction of Isobutanol (Iso-BuOH) with an Acid Catalyst to Produce Isooctenes

The feedstock was 85 wt. % isobutanol/15 wt. % water. Abbreviations: Press is pressure; Cony is conversion; Sel is selectivity.

| Example Number | Catalyst | Catalyst Loading (mg) | Time (hr) | Temp (C.) | $N_2$ Press (MPa) | iso-BuOH % Conv | Isooctenes % Sel |
|---|---|---|---|---|---|---|---|
| 1 | Amberlyst ® 15 | 107 | 2 | 200 | 6.6 | 53.5 | 54.1 |
| 2 | 13% Nafion ®/$SiO_2$ | 119 | 2 | 200 | 6.6 | 4.0 | 2.2 |
| 3 | CBV-3020E | 102 | 2 | 200 | 6.6 | 49.8 | 45.6 |
| 4 | H-Mordenite | 103 | 2 | 200 | 6.6 | 47.0 | 42.7 |
| 5 | Sulfuric Acid | 54 | 2 | 200 | 6.6 | 96.3 | 61.3 |

As those skilled in the art of catalysis know, when working with any catalyst, the reaction conditions need to be optimized. Examples 1 to 5 show that the indicated catalysts were capable under the indicated conditions of producing the product isooctenes. Some of the catalysts shown in Examples 1 to 5 were ineffective when utilized at suboptimal conditions (e.g., lower temperature) (data not shown).

The invention claimed is:

1. A process for production of a recovered isooctene from renewable sources comprising:
    (a) providing a feedstock derived from a renewable source to a recombinantly engineered microorganism;
    (b) fermenting the feedstock with the recombinantly engineered microorganism, thereby forming isobutanol;
    (c) recovering at least a portion of the isobutanol;
    (d) contacting at least a portion of the recovered isobutanol with an acid catalyst in the presence of water to produce a first reaction product that comprises at least one isooctene,
    wherein the recombinantly engineered microorganism is engineered to express a biosynthetic pathway comprising substrate to product conversions that include:
    pyruvate to acetolactate;
    acetolactate to 2,3-dihydroxyisovalerate;
    2,3-dihydroxyisovalerate to α-ketoisovalerate;
    α-ketoisovalerate to isobutyraldehyde; and
    isobutyraldehyde to the isobutanol.

2. The process of claim 1, wherein the acid catalyst can be a homogeneous or heterogeneous catalyst.

3. The process of claim 2, wherein the acid catalyst is a homogeneous catalyst selected from the group consisting of inorganic acids, organic sulfonic acids, heteropolyacids, fluoroalkyl sulfonic acids, metal sulfonates, metal trifluoroacetates, compounds thereof, and combinations thereof.

4. The process of claim 3, wherein the homogeneous catalyst is selected from the group consisting sulfuric acid, fluorosulfonic acid, phosphoric acid, p-toluenesulfonic acid, benzenesulfonic acid, hydrogen fluoride, phosphotungstic acid, phosphomolybdic acid, and trifluoromethanesulfonic acid.

5. The process of claim 2, wherein the acid catalyst is a heterogeneous catalyst selected from the group consisting of heterogeneous heteropolyacids, natural clay minerals, cation exchange resins, metal oxides, mixed metal oxides, metal sulfides, metal sulfates, metal sulfonates, metal nitrates, metal phosphates, metal phosphonates, metal molybdates, metal tungstates, metal borates, zeolites, and combinations thereof.

6. The process of claim 1, further comprising:
(e) contacting the isooctene with at least one hydrogenation catalyst in the presence of hydrogen to produce a second reaction product comprising at least one isooctane; and
(f) recovering the at least one isooctane from the second reaction product to produce a recovered isooctane.

7. The process of claim 6, further comprising:
(g) adding the recovered isooctane to a transportation fuel.

8. The process of claim 6, wherein the hydrogenation catalyst comprises a principal component that is a metal selected from the group consisting of palladium, ruthenium, rhenium, rhodium, iridium, platinum, nickel, cobalt, copper, iron, osmium, compounds thereof, and combinations thereof.

9. The process of claim 1, further comprising:
(e) contacting the isooctene with water in the presence of at least one acid catalyst to produce a second reaction product comprising at least one isooctanol; and
(f) recovering the at least one isooctanol from the second reaction product to produce a recovered isooctanol.

10. The process of claim 9, further comprising:
(g) adding the recovered isooctanol to a transportation fuel.

11. The process of claim 9, wherein the acid catalyst of (e) can be a homogeneous or heterogeneous catalyst.

12. The process of claim 11, wherein the acid catalyst is a homogeneous catalyst selected from the group consisting of inorganic acids, organic sulfonic acids, heteropolyacids, fluoroalkyl sulfonic acids, metal sulfonates, metal trifluoroacetates, compounds thereof, and combinations thereof.

13. The process of claim 12, wherein the homogeneous catalyst is selected from the group consisting of sulfuric acid, fluorosulfonic acid, phosphoric acid, p-toluenesulfonic acid, benzenesulfonic acid, hydrogen fluoride, phosphotungstic acid, phosphomolybdic acid, and trifluoromethanesulfonic acid.

14. The process of claim 11, wherein the acid catalyst is a heterogeneous catalyst selected from the group consisting of heterogeneous heteropolyacids, natural clay minerals, cation exchange resins, metal oxides, mixed metal oxides, metal sulfides, metal sulfates, metal sulfonates, metal nitrates, metal phosphates, metal phosphonates, metal molybdates, metal tungstates, metal borates, zeolites, and combinations thereof.

15. The process of claim 1, further comprising:
(e) contacting the isooctene with at least one acid catalyst in the presence of at least one straight-chain or branched $C_1$ to $C_5$ alcohol to produce a second reaction product comprising at least one isooctyl alkyl ether; and
(f) recovering the at least one isooctyl alkyl ether from the second reaction product to produce a recovered isooctyl alkyl ether.

16. The process of claim 15, further comprising:
(g) adding the recovered isooctyl alkyl ether to a transportation fuel.

17. The process of claim 15, wherein the acid catalyst of (e) can be a homogeneous or heterogeneous catalyst.

18. The process of claim 17, wherein the acid catalyst is a homogeneous catalyst selected from the group consisting of inorganic acids, organic sulfonic acids, heteropolyacids, fluoroalkyl sulfonic acids, metal sulfonates, metal trifluoroacetates, compounds thereof, and combinations thereof.

19. The process of claim 18, wherein the homogeneous catalyst is selected from the group consisting sulfuric acid, fluorosulfonic acid, phosphoric acid, p-toluenesulfonic acid, benzenesulfonic acid, hydrogen fluoride, phosphotungstic acid, phosphomolybdic acid, and trifluoromethanesulfonic acid.

20. The process of claim 17, wherein the acid catalyst is a heterogeneous catalyst selected from the group consisting of heterogeneous heteropolyacids, natural clay minerals, cation exchange resins, metal oxides, mixed metal oxides, metal sulfides, metal sulfates, metal sulfonates, metal nitrates, metal phosphates, metal phosphonates, metal molybdates, metal tungstates, metal borates, zeolites, and combinations thereof.

21. A process for production of a recovered butene from renewable sources comprising:
(a) providing a feedstock derived from a renewable source to a recombinantly engineered microorganism;
(b) fermenting the feedstock with the recombinantly engineered microorganism, thereby forming isobutanol;
(c) recovering at least a portion of the isobutanol;
(d) contacting at least a portion of the recovered isobutanol with an acid catalyst in the presence of water to produce a reaction product that comprises at least one butene; and
(e) recovering the at least one butene from the reaction product to produce a recovered butene,
wherein the recombinantly engineered microorganism is engineered to express a biosynthetic pathway comprising substrate to product conversions that include:
pyruvate to acetolactate;
acetolactate to 2,3-dihydroxyisovalerate;
2,3-dihydroxyisovalerate to α-ketoisovalerate;
α-ketoisovalerate to isobutyraldehyde; and
isobutyraldehyde to the isobutanol.

22. The process of claim 21, wherein the acid catalyst can be a homogeneous or heterogeneous catalyst.

23. The process of claim 22, wherein the acid catalyst is a homogeneous catalyst selected from the group consisting of inorganic acids, organic sulfonic acids, heteropolyacids, fluoroalkyl sulfonic acids, metal sulfonates, metal trifluoroacetates, compounds thereof, and combinations thereof.

24. The process of claim 23, wherein the homogeneous catalyst is selected from the group consisting sulfuric acid, fluorosulfonic acid, phosphoric acid, p-toluenesulfonic acid, benzenesulfonic acid, hydrogen fluoride, phosphotungstic acid, phosphomolybdic acid, and trifluoromethanesulfonic acid.

25. The process of claim 22, wherein the acid catalyst is a heterogeneous catalyst selected from the group consisting of heterogeneous heteropolyacids, natural clay minerals, cation exchange resins, metal oxides, mixed metal oxides, metal sulfides, metal sulfates, metal sulfonates, metal nitrates, metal phosphates, metal phosphonates, metal molybdates, metal tungstates, metal borates, zeolites, and combinations thereof.

* * * * *